United States Patent
Molino

(10) Patent No.: US 7,479,560 B2
(45) Date of Patent: *Jan. 20, 2009

(54) CREATINE PYROGLUTAMIC ACID SALTS AND METHODS FOR THEIR PRODUCTION AND USE IN INDIVIDUALS

(75) Inventor: Michele Molino, Mississauga (CA)

(73) Assignee: New Cell Formulations, Ltd., Mississauga, ON (CA)

(*) Notice: Subject to any disclaimer, the term of this patent is extended or adjusted under 35 U.S.C. 154(b) by 0 days.

This patent is subject to a terminal disclaimer.

(21) Appl. No.: 11/776,049

(22) Filed: Jul. 11, 2007

(65) Prior Publication Data

US 2008/0064737 A1    Mar. 13, 2008

Related U.S. Application Data

(63) Continuation of application No. 11/530,601, filed on Sep. 11, 2006, now Pat. No. 7,329,763.

(51) Int. Cl.
C07D 239/22 (2006.01)

(52) U.S. Cl. .................. 544/314; 514/269; 514/274
(58) Field of Classification Search .............. 548/530; 544/314; 514/554
See application file for complete search history.

(56) References Cited

U.S. PATENT DOCUMENTS

| 5,925,378 A | 7/1999 | Carnazzo |
| 5,973,199 A | 10/1999 | Negrisoli et al. |
| 6,166,249 A | 12/2000 | Pischel et al. |
| 6,211,407 B1 | 4/2001 | Thomson |
| 6,838,562 B2 * | 1/2005 | Abraham et al. ............. 544/314 |
| 6,861,554 B2 | 3/2005 | Buononato |
| 7,329,763 B1 * | 2/2008 | Molino et al. ............... 548/530 |

OTHER PUBLICATIONS

Harris RC et al. Elevation of creatine in resting and exercised muscle of normal subjects by creatine supplementation, Clin Sci (Lond). Sep. 1992;83(3):367-74.
Greenhaff PL et al. Effect of oral creatine supplementation on skeletal muscle phosphocreatine resynthesis. Am J Physiol. May 1994;266(5 pt 1);E725-30.
Greenhaff PL et al. Influence of oral creatine supplementation of muscle torque during repeated bouts of maximal voluntary exercise in man. Clin Sci (Lond). May 1993;84(5):565-7.
Sestili P et al. Creatine supplementation affords cytoprotection in oxidatively injured cultured mammalian cells via direct antioxidant activity. Free Radic Biol Med. Mar. 1, 2006;40(5):837-49.
Zhu S et al. Prophylactic creatine administration mediates neuroprotection in cerebral ischemia in mice. J Neurosci. Jun. 30, 2004;24(26):5909-12.
Drago F et al. Pyroglutamic acid improves learning and memory capacities in old rats. Funct Neurol, Apr.-Jun. 1988;3(2):137-43.
Grioli S et al. Pyroglutamic acid improves the age associated memory impairment. Fundam Clin Pharmacol, 1990;4(2): 169-73.
PCT International Search Report, International Application No. PCT/CA2006/001491, filed Sep. 11, 2006.

* cited by examiner

Primary Examiner—Daniel M Sullivan
Assistant Examiner—Sudhakar Katakam

(57) ABSTRACT

The present invention relates to a method of production and the use of a compositional ingredient. Specifically, the present invention relates to hydrosoluble stable organic salts of creatine and pyroglutamic acid. The compositional ingredient may be useful for the regulation of athletic and cognitive functions.

5 Claims, No Drawings

CREATINE PYROGLUTAMIC ACID SALTS AND METHODS FOR THEIR PRODUCTION AND USE IN INDIVIDUALS

RELATED APPLICATIONS

This application is a continuation application of co-pending U.S. application Ser. No. 11/530,601, filed Sep. 11, 2006, the entire contents of which are incorporated by this reference.

FIELD OF THE INVENTION

The present invention relates to hydrosoluble stable organic salts of creatine and pyroglutamic acid. The present invention discloses a composition and a method for production of the composition. Additionally, the invention relates to administration of the compositional to a mammal as a method to improve athletic and cognitive functions.

BACKGROUND OF THE INVENTION

Creatine monohydrate is a commonly used supplement. Creatine monohydrate is soluble in water at a rate of 75 ml of water per gram of creatine. Ingestion of creatine monohydrate thereof requires large amounts of water to also be ingested. Additionally, in aqueous solutions, creatine converts to creatinine via an irreversible, pH-dependent, non-enzymatic reaction. Aqueous and alkaline solutions contain an equilibrium mixture of creatine and creatinine. In acidic solutions, on the other hand, the formation of creatinine is complete. Creatinine is devoid of the ergogenic beneficial effects of creatine and is typically excreted in the urine. It is therefore desirable to provide, for use in individuals, e.g. animals and humans, forms and derivatives of creatine with improved characteristics such as stability and solubility. Furthermore, it would be advantageous to do so in a manner that provides additional functionality compared to creatine monohydrate alone.

Hydrosoluble creatine monohydrate salts are obtainable and have been described elsewhere. For instance, U.S. Pat. No. 5,973,199, incorporated herein in its entirety by reference, purports to describe hydrosoluble organic salts of creatine as single combination of one mole of creatine monohydrate with one mole of the following organic acids: citrate, malate, fumarate, tartarate, and malate.

U.S. Pat. No. 5,925,378, incorporated herein in its entirety by reference, purports to describe a form of a creatine salt as a combination of one mole of creatine with one mole of citric acid.

U.S. Pat. No. 6,211,407, incorporated herein in its entirety by reference, purports to describe dicreatine and tricreatine citrate and methods of making the same. Salts are reported to be a combination of two and three moles of creatine monohydrate with one mole of citric acid, respectively. In addition, dicreatine and tricreatine citrate are claimed to be stable in acidic solution, in a guise to prevent or impede the formulation of creatine to creatinine.

U.S. Pat. No. 6,166,249, incorporated herein in its entirety by reference, purports to describe a creatine pyruvic acid salt where the ratio of creatine to pyruvate is 1:1 and the creatine pyruvate contains 1-10 molecules of water.

U.S. Pat. No. 5,973,199, incorporated herein in its entirety by reference, purports to describe a method of producing a creatine malate salt with a melting point of between 128 and 129° C. The patent also purports to describe a method of producing a creatine citrate salt with a melting point between 112 and 114° C.

U.S. Pat. No. 6,838,562, incorporated herein in its entirety by reference, purports to describe a process for the synthesis of mono, di, or tricreatine orotic acid, thioorotic acid, and dihydroorotic acid salts.

U.S. Pat. No. 6,861,554, incorporated herein in its entirety by reference, purports to describe a formula, a novel salt, creatine taurinate, and the compositions containing same (health foods, compositions or drugs).

SUMMARY OF THE INVENTION

The present invention discloses a hydrosoluble stable organic salt of creatine and D,L-pyroglutamic acid, i.e., creatine pyroglutamate, characterized by high water solubility, i.e., from 2 to 25 times higher than that of creatine itself and having a melting point about 160 to about 168° C. with a molecular weight range of about 242 to about 262. The present invention describes processes for the preparation of the salt and methods for administering the salt to a mammal, such as a human.

The present invention also discloses methods of using effective amounts of creatine pyroglutamate for the regulation of athletic and cognitive functions in mammals, and for affording preventative neuroprotection and preservation of cognitive activity in aging, neurodegenerative disease, reperfusion insult, ischemic brain infarction and cerebral ischemia.

DETAILED DESCRIPTION OF THE INVENTION

In the following description, for the purposes of explanation, numerous specific details are set forth in order to provide a thorough understanding of the present invention. It will be apparent, however, to one skilled in the art that the present invention may be practiced without these specific details.

The present invention relates to the production and use of hydrosoluble stable organic salts of creatine and pyroglutamic acid. The organic salts may be useful as a compositional ingredient for regulating athletic and cognitive functions in addition to post-insult recovery.

As used herein, "athletic functions" refers to the sum of physical attributes which can be dependent to any degree on skeletal muscle contraction. For example, athletic functions include, but are not limited to, maximal muscular strength, muscular endurance, running speed and endurance, swimming speed and endurance, throwing power, lifting and pulling power.

As used herein, "cognitive functions" refers to any mental component of brain function. For example, cognitive functions include, but are not limited to, attention, concentration, memory and focus.

As used herein, "Creatine" refers to the chemical N-methyl-N-guanyl Glycine, (CAS Registry No. 57-00-1), also known as, (alpha-methyl guanido) acetic acid, N-(aminoiminomethyl)-N-glycine, Methylglycocyamine, Methylguanidoacetic Acid, or N-Methyl-N-guanylglycine. Additionally, as used herein, "Creatine" also includes derivatives of Creatine such as esters, and amides, and salts, as well as other derivatives, including derivatives that become active upon metabolism. Furthermore, Creatinol (CAS Registry No. 6903-79-3), also known as Creatinol-O-Phosphate, N-methyl-N-(beta-hydroxyethyl)guanidine O-Phosphate, or 2-(carbamimidoyl-methyl-amino)ethoxyphosphonic acid, is henceforth in this disclosure considered to be a Creatine derivative.

Creatine

Creatine is a naturally occurring amino acid derived from the amino acids glycine, arginine, and methionine. Although it is found in meat and fish, it is also synthesized by humans. Creatine is predominantly used as a fuel source in muscle. About 65% of Creatine is stored in muscle as Phosphocreatine (Creatine bound to a Phosphate molecule). Muscular contractions are fueled by the dephosphorylation of adenosine triphosphate (ATP) to produce adenosine diphosphate (ADP) and without a mechanism to replenish ATP stores, the supply of ATP would be totally consumed in 1-2 seconds. Phosphocreatine serves as a major source of Phosphate from which ADP is regenerated to ATP. Six seconds following the commencement of exercise, muscular concentrations of Phosphocreatine drop by almost 50% and Creatine supplementation has been shown to increase the concentration of Creatine in the muscle (Harris R C, Soderlund K, Hultman E. Elevation of creatine in resting and exercised muscle of normal subjects by creatine supplementation. Clin Sci (Lond). 1992 September; 83(3):367-74) and further said supplementation enables an increase in the resynthesis of Phosphocreatine (Greenhaff P L, Bodin K, Soderlund K, Hultman E. Effect of oral creatine supplementation on skeletal muscle phosphocreatine resynthesis. Am J Physiol. 1994 May; 266(5 Pt 1):E725-30) leading to a rapid replenishment of ATP within the first two minutes following the commencement of exercise. It may be through this mechanism that Creatine can improve strength and reduce fatigue (Greenhaff P L, Casey A, Short A H, Harris R, Soderlund K, Hultman E. Influence of oral creatine supplementation of muscle torque during repeated bouts of maximal voluntary exercise in man. Clin Sci (Lond). 1993 May; 84(5): 565-71). Furthermore, there is evidence that Creatine may have antioxidant properties that may additionally aid post-exercise muscle recovery and recovery from neuronal insults (Sestili P, Martinelli C, Bravi G, Piccoli G, Curci R, Battistelli M, Falcieri E, Agostini D, Gioacchini A M, Stocchi V. Creatine supplementation affords cytoprotection in oxidatively injured cultured mammalian cells via direct antioxidant activity. Free Radic Biol Med. 2006 Mar. 1; 40(5):837-49).

Thus, creatine supplementation may result in positive physiologic effects on skeletal muscle, such as: performance improvements during brief high-intensity anaerobic exercise, increased strength and ameliorated body composition in physically active subjects.

Creatine also mediates remarkable neuroprotection in experimental models of amyotrophic lateral sclerosis, Huntington's disease, Parkinson's disease, and traumatic brain injury. Also, oral creatine administration to experimental animals has been shown to result in a remarkable reduction in ischemic brain infarction and neuroprotection after cerebral ischemia (Zhu S, Li M, Figueroa B E, Liu A, Stavrovskaya I G, Pasinelli P, Beal M F, Brown R H Jr, Kristal B S, Ferrante R J, Friedlander R M. Prophylactic creatine administration mediates neuroprotection in cerebral ischemia in mice. J Neurosci. 2004 Jun. 30; 24(26):5909-12).

Pyroglutamic Acid

Pyroglutamic acid (CAS 98-79-3) is naturally occurring amino acid derived from L-glutamic acid and involved in glutathione metabolism. Pyroglutamic acid crosses the blood-brain barrier and is found in high levels in the brain where it is thought to act in improving cognitive function. Pyroglutamate is generally available as arginine pyroglutamate wherein, the primary claim made for this arginine salt of pyroglutamic acid relates to its cognitive enhancement capacity. It is asserted by some that this substance can help overcome memory defects induced by alcohol abuse and in those with some forms of dementia.

Pyroglutamic acid has been shown to improve specific aspects of cognitive function in rats (Drago F, Valerio C, D'Agata V, Astuto C, Spadaro F, Continella G, Scapagnini U. Pyroglutamic acid improves learning and memory capacities in old rats. Funct Neurol. April-June 1988; 3(2):137-43). In humans pyroglutamic acid improves age-associated memory impairment (Grioli S, Lomeo C, Quattropani M C, Spignoli G, Villardita C. Pyroglutamic acid improves the age associated memory impairment. Fundam Clin Pharmacol. 1990; 4(2):169-73).

Creatine Pyroglutamate

Creatine Pyroglutamate combines the muscle-enhancing and neuroprotective effects of creatine with the cognition-enhancing activity afforded by pyroglutamic acid. The novel organic compound can be used in sports nutrition as an ergogenic aid to increase strength, muscle volume and size, while affording improved capacity of concentration and mental focus during physical exertion. Also, this creatine salt can find employment in metabolic nutrition by defending against ischemic brain infarction and affording neuroprotection after cerebral ischemia.

The salt is prepared by reacting equimolar amounts of creatine and D,L-pyroglutamic acid in aqueous or hydroalcoholic concentrated solution or in a water-immiscible solvent (or mixture of solvents), at temperatures ranging from room temperature to 50° C. Additionally, the reaction may be induced to proceed through the melting of pyroglutamic acid, forming a liquid reaction medium and adding creatine, followed by a subsequent extraction of the salt from the reaction mixture with cyclohexane.

Creatine Pyroglutamate (2-(1-methylguanidino)acetyl)oxonium (S)-5-oxopyrrolidine-2-carboxylate Chemical Formula: $C_9H_{16}N_4O_5$
Exact Mass: 260.11
Molecular Weight: 260.25
m/z: 260.11 (100.0%), 261.12 (10.1%), 262.12 (1.5%), 261.11 (1.5%) Elemental Analysis: C, 41.54; H, 6.20; N, 21.53; O, 30.74

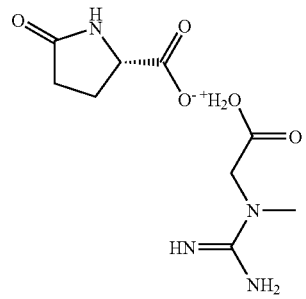

(2-(1-methylguanidino)acetyl)oxonium pyroglutamate

FIG 1. Schematic Reprsentation of Creatine Pyroglutamate

According to a preferred embodiment, the aforementioned salt can be prepared by reacting creatine with an equimolar amount of D,L-pyroglutamic acid in ethyl acetate (or in a mixture of equal parts ethyl acetate and ethanol) until complete formation of the salt. The solution can be optionally concentrated and, upon cooling, the crystallized salts are filtered and washed with ethyl acetate (or a mixture of ethyl acetate and ethanol). Alternatively, the procedure can be carried on by reacting excess D,L-pyroglutamic acid with creatine in ethyl acetate (or a mixture of ethyl acetate and ethanol).

Advantageously, creatine pyroglutamate can be used as a composition, either alone or as part of a larger composition containing any number of additional ingredients. It will be apparent to those skilled in the art as to which specific ingredients may be included in such compositions.

Furthermore, creatine pyroglutamate, as a compositional ingredient may be administered in any form common in the art. For example, the compositional ingredient may be administered in the form of a powder to be mixed in liquid or in a solid dosage form such as a tablet, capsule or caplet. Additionally, creatine pyroglutamate may be suspended or dissolved in any pharmaceutically acceptable carrier or vehicle medium for injection. As such, it may be combined with any number of commonly accepted excipients, as is regular practice in the art.

The following examples illustrate processes for synthesis and characterization of creatine pyroglutamate. The following examples should not be considered as limiting the scope of the present invention.

EXAMPLES

Example 1

Experiment 1

Procedure:
1) 12.912 g (0.1 mol) of L-pyroglutamic acid (99% purity) were added to 100 ml of ethyl acetate in a beaker. A stir bar was placed inside and the mixture stirred for ~10 min.
2) 14.9 g (0.1 mol) of creatine monohydrate were added to the stirred suspension at 20-25° C. and the mixture allowed to stir for ~3 hours at 25° C.
3) The white, finely crystalline product obtained was separated out by filtering, the filtrate discarded and the crystalline residue collected.
4) A sample of the solid residue (crystalline product) was suspended in 25 ml ethyl acetate and then filtered.
5) The residue (from step 4) was suspended in another 25 ml ethyl acetate and filtered again.
6) The unwashed product (residue from step 3) and the washed product were placed in two separate beakers and the solvent allowed to evaporate overnight.

Solubility Test

A test was performed to compare the solubility of creatine monohydrate to the washed product obtained in Experiment 1. The procedure was as follows:
a) 2 g of each substance were placed in two separate beakers with 75 ml of distilled water each
b) The mixtures were stirred mechanically for ~5 min.
c) Upon visual inspection, the experimental product dissolved completely but the creatine monohydrate did not dissolve very well.
d) pH measurements:
pH of 2 g creatine monohydrate in 75 ml H$_2$O=~7.00
pH of 2 g unwashed product in 75 ml H$_2$O=~3.00
pH of 2 g pyroglutamic acid in 75 ml H$_2$O=~2.00
e) To see if lowering the pH of creatine monohydrate solution would increase solubility, some pyroglutamic acid was added and the creatine monohydrate dissolved.

Melting Point

The melting range of the washed product was determined to be within 160-166° C.

The melting range of the washed product was determined to be within 162-168° C.

Example 2

Experiment 2

Procedure:
1) 12.912 g (0.1 mol) of L-pyroglutamic acid (99% purity) were added to 20 ml distilled H$_2$O in a beaker. The mixture was heated to 30° C. and stirred mechanically for ~15 min.
2) 14.9 g (0.1 mol) of monohydrate creatine were added to the mixture and allowed to stir for ~30 min until concentrated (note that the mixture was extremely thick, i.e., slurry-like consistency) and cooled to 5° C.
3) The product mixture was filtered and the solid residue collected.
4) The collected product was suspended in 50 ml absolute ethanol to remove any residual water.
5) The mixture was filtered and the solid crystalline residue recovered.
6) The collected solid crystalline residue was placed in a beaker and allowed to dry overnight (i.e., ethanol evaporation).

Solubility Test

A test was performed to compare the solubility of creatine monohydrate to the product obtained in Experiment 2. The procedure was as follows:
a) 2 g of the dried product (from step 6) were added in a beaker to 75 ml distilled H$_2$O and stirred for ~5 min. The crystals completely dissolved within 5 min.
b) 2 g of creatine monohydrate were added in a beaker to 75 ml distilled H$_2$O and stirred. After 30 min of stirring, there was still a considerable amount of solids that did not dissolve.
c) pH measurement: The pH of the experimental product (2 g in 75 ml H$_2$O) was measured at 3.09.

Melting Point

The melting range of the crystalline product from Experiment 2 was determined to be within 162-168° C.

What is claimed:
1. A compound having the formula:

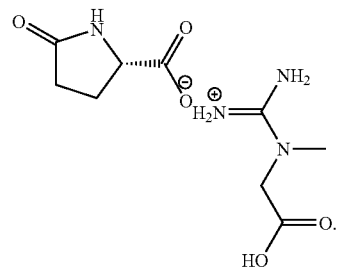

2. The structure according to claim 1 wherein the Melting Range is from about 160 to about 168° C.

3. The structure according to claim 1 wherein the claimed structure is a stable hydrosoluble organic salt of creatine and D,L-pyroglutamic acid, creatine pyroglutamate.

4. The structure according to claim 1 wherein the claimed structure is a creatine salt having enhanced solubility in aqueous and organic mediums, wherein said salt is from 2 to 25 times more soluble than creatine.

5. The structure according to claim 1 wherein the claimed structure is a creatine salt having increased absorbability and tissue bioavailability in humans and animals compared to creatine monohydrate.

* * * * *